US012576284B2

(12) United States Patent
Hirvonen et al.

(10) Patent No.: US 12,576,284 B2
(45) Date of Patent: Mar. 17, 2026

(54) METHOD AND APPARATUS FOR FACILITATING OPTIMIZING AND ADMINISTERING AN ENERGY THERAPY TREATMENT PLAN

(71) Applicant: Siemens Healthineers International AG, Steinhausen (CH)

(72) Inventors: Petri Hirvonen, Espoo (FI); Matti Ropo, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 226 days.

(21) Appl. No.: 18/369,623

(22) Filed: Sep. 18, 2023

(65) Prior Publication Data

US 2025/0090866 A1    Mar. 20, 2025

(51) Int. Cl.
A61N 5/10    (2006.01)

(52) U.S. Cl.
CPC ......... A61N 5/1069 (2013.01); A61N 5/1031 (2013.01); *A61N 2005/1074* (2013.01); *A61N 2005/1087* (2013.01)

(58) Field of Classification Search
None
See application file for complete search history.

(56) References Cited

U.S. PATENT DOCUMENTS

| | | |
|---|---|---|
| 11,938,341 B2 | 3/2024 | Peltola |
| 2020/0261743 A1* | 8/2020 | Joe Anto .............. A61N 5/1037 |
| 2023/0191149 A1 | 6/2023 | Ropo |
| 2023/0372736 A1* | 11/2023 | Duan .................... A61N 5/1031 |

OTHER PUBLICATIONS

Extended European Search Report and related European Patent Application No. 24200108.9 dated Jan. 31, 2025; 8 pages.
Harrison, Nathan et al.; novel inverse algorithm to solve IPO-IMPT of proton Flash therapy with sparse filters, arxiv.org, Cornell University Library, 201 Olin Library Cornell University Ithaca, NY 14853, Apr. 19, 2023 (Apr. 19, 2023), XP091488399.
Liu, Chenbin et al.; Robust Optimization for Intensity Modulated Proton Therapy to Redistribute High Linear Energy Transfer from Nearby Critical Organs to Tumors in Head and Neck Cancer; International Journal of Radiation: Oncology Biology Physics, Pergamon Press, USA, vol. 107, No. 1, Jan. 25, 2020 (Jan. 25, 2020), pp. 181-192, XP086129574, ISSN: 0360-3016, DOI: 10.1016/J.IJROBP.2020.01.013 [retrieved on Jan. 25, 2020].
Liu, Ruirui et al.; An Integrated Physical Optimization Framework for Proton Stereotactic Body Radiation Therapy Flash Treatment Planning Allows Dose, Dose Rate, and Linear Energy Transfer Optimization Using Paitent-Specific Ridge Filters; International Journal of Radiation: Oncology Biology Physics, Pergamon Press, USA, vol. 116, No. 4, Jan. 21, 2023 (Jan. 21, 2023), pp. 949-959, XP087343518, ISSN: 0360-3016, DOI: 10.1016/J.IJROBP.2023.01.048 [retrieved on Feb. 1, 2023].

* cited by examiner

*Primary Examiner* — Marcus H Taningco
(74) *Attorney, Agent, or Firm* — Fitch, Even, Tabin & Flannery LLP

(57)    ABSTRACT

A control circuit presents, via a user interface, linear energy transfer information that corresponds to optimizing an energy therapy treatment plan (such as a proton therapy treatment plan). Upon detecting certain user input, the control circuit can respond by accessing a precomputed influence matrix to provide corresponding accessed information and then present modified linear energy transfer information via the user interface as a function, at least in part, of that accessed information.

20 Claims, 3 Drawing Sheets

_200_

1

METHOD AND APPARATUS FOR FACILITATING OPTIMIZING AND ADMINISTERING AN ENERGY THERAPY TREATMENT PLAN

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, proton therapy comprises an important component of many treatment plans for reducing or eliminating unwanted tumors. Proton radiation therapy employs protons, which are positively charged subatomic particles found in the nucleus of atoms, as opposed to the more commonly used X-rays or photons in traditional radiation therapy. Proton therapy facilitates the precise targeting and delivery of energy to tumors while often minimizing damage to surrounding healthy tissues.

Imaging techniques such as computed tomography scans or magnetic resonance images can serve to precisely map a tumor's location, size, and shape. Using this information, a treatment plan can be developed that determines optimal angles and energies for delivering the proton beams.

Linear energy transfer describes the energy that is deposited per unit distance by an ionizing particle. This roughly corresponds to the frequency of interactions along the particle's trajectory. For protons, the linear energy transfer tends to be concentrated at a point typically referred to as the Bragg peak. A higher linear energy transfer typically correlates to more killed or damaged cells. The dose may be low in a particular region but the linear energy transfer may nevertheless be high. This means that, for example, an organ-at-risk may appear to be receiving a low dose while the organ also receives a relatively high linear energy transfer that can result in possibly surprising damage to that organ-at-risk.

The applicant has determined that it can be useful to provide a treatment planner with information regarding linear energy transfer to thereby allow that information to be better taken into account when optimizing a dose.

BRIEF DESCRIPTION OF THE DRAWINGS

The above needs are at least partially met through provision of the method and apparatus for facilitating optimizing and administering an energy therapy treatment plan described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments, a control circuit presents, via a user interface, linear energy transfer information that corresponds to optimizing an energy therapy treatment plan (such as a proton therapy treatment plan). Upon detecting certain user input, the control circuit can respond by accessing a precomputed influence matrix to provide corresponding accessed information and then present modified linear energy transfer information via the user interface as a function, at least in part, of that accessed information.

These teachings will accommodate a variety of approaches as regards detecting the aforementioned user input. That user input may comprise, for example, the movement of a displayed cursor and/or user-based painting of a displayed patient portion (such as a tumor or an organ-at-risk). As another example, these teachings will accommodate detecting a user's spot-based modification.

The aforementioned precomputed influence matrix may comprise, for example, precomputed linear energy transfer contributions (if desired, for each voxel on a voxel-by-voxel basis). By one approach, the foregoing may comprise each spot's linear energy contributions for each voxel.

So configured, these teachings provide a practical and flexible approach for visualizing and extracting some linear energy transfer information and for taking such information into account when optimizing the dose to be administered notwithstanding that, ordinarily, linear energy transfer calculation is typically viewed as a rather noninteractive and indirect process for many users.

Figure 1:
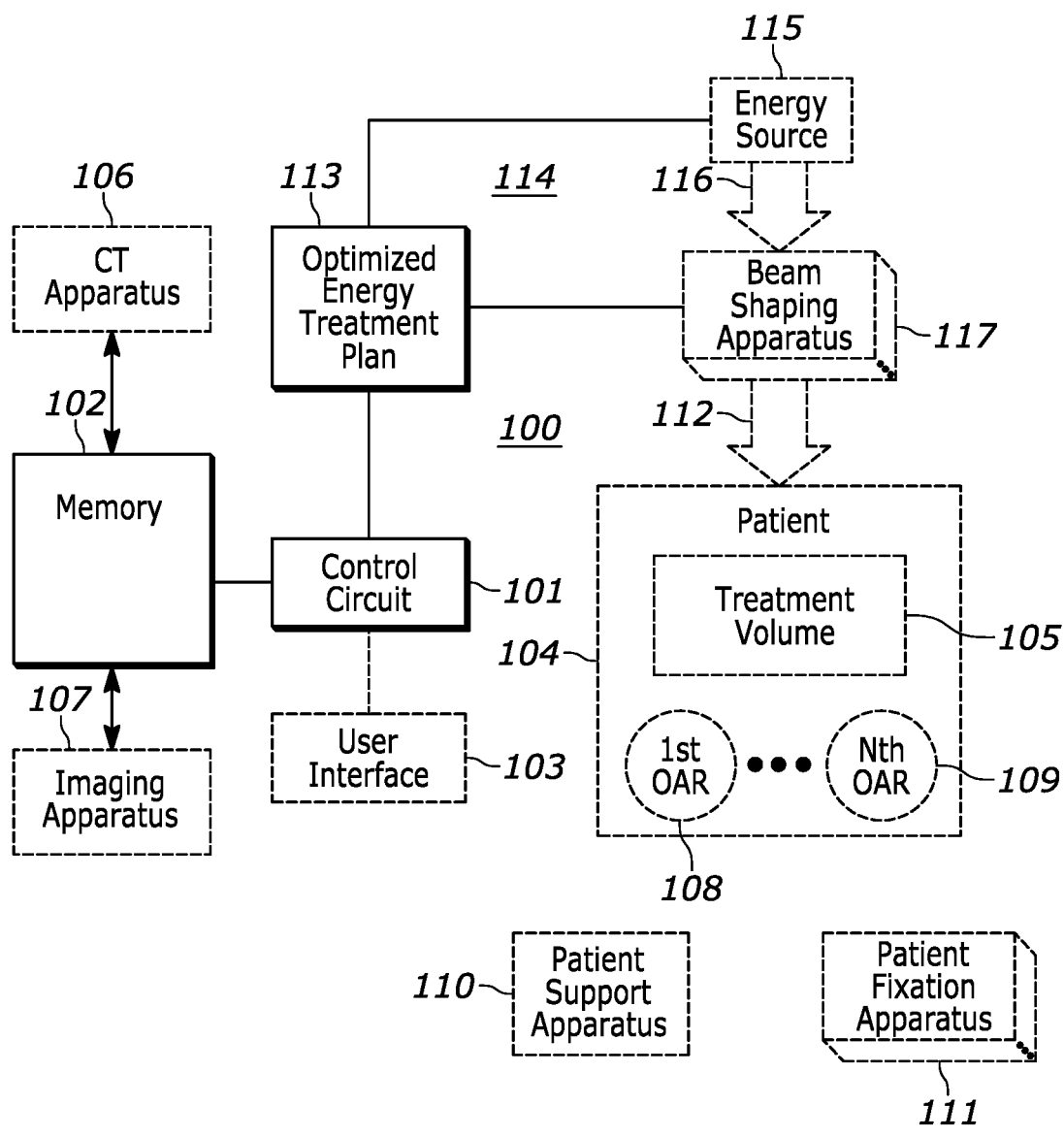
FIG. 1 comprises a block diagram as configured in accordance with various embodiments of these teachings.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular energy treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized energy treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. For the sake of the present description, but without intending to suggest any limitations in these regards, the energy-based treatment platform 114 includes an energy source such as an energy source 115 of accelerated protons 116.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway. As one illustrative example, the energy source 115 can comprise a particle accelerator such as a cyclotron or a synchrotron.

A typical energy-based treatment platform 114 may also include one or more support apparatuses 110 (such as a couch) to support the patient 104 during the treatment session, one or more patient fixation apparatuses 111, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
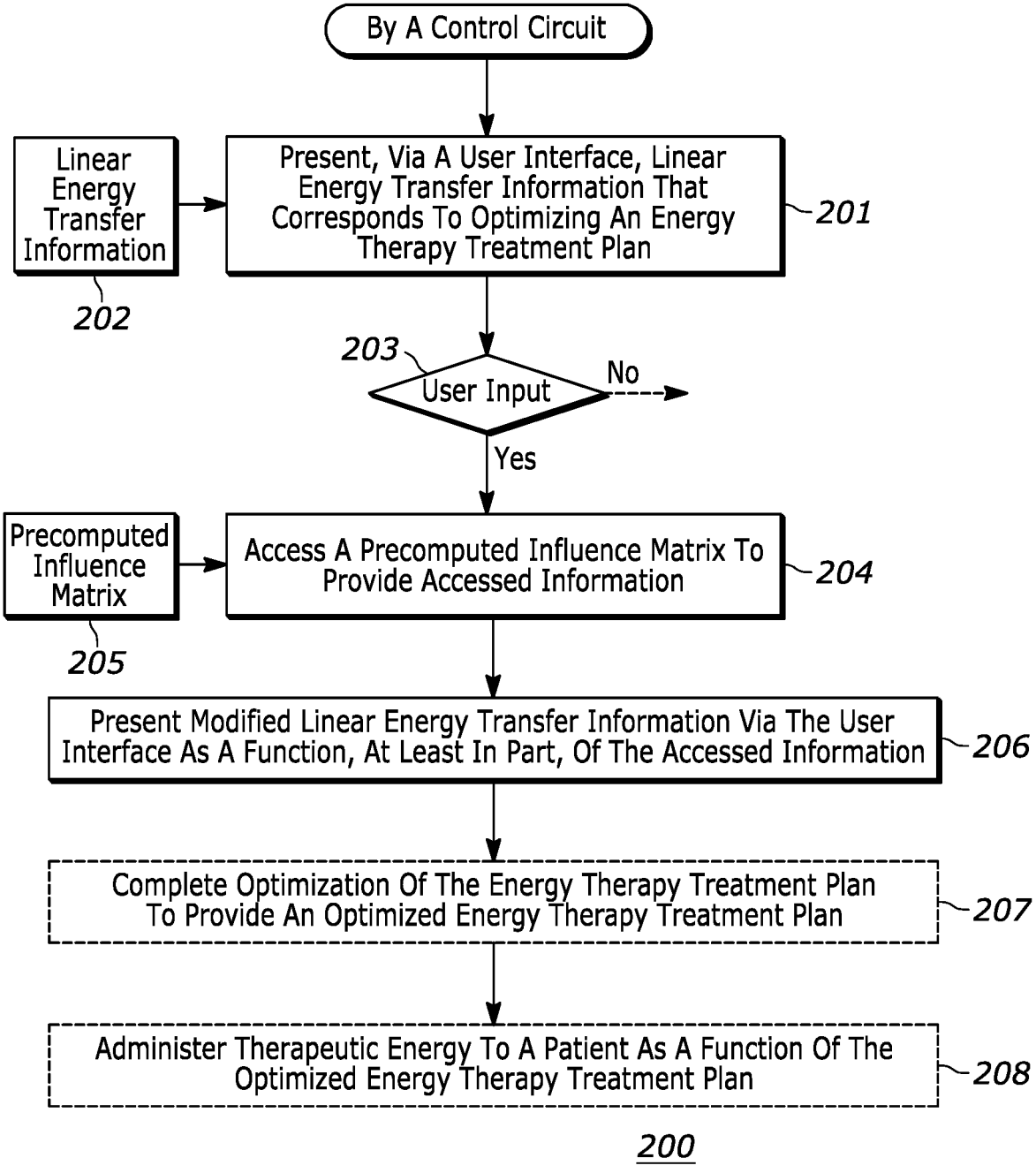
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized energy treatment plan 113 to thereby facilitate treating a particular patient with therapeutic energy using a particular energy treatment platform per that optimized energy treatment plan.

At block 201, this process 200 presents (for example, via the aforementioned user interface 103), linear energy transfer information 202 that corresponds to optimizing an energy therapy treatment plan. For the sake of an illustrative example, this description will presume this energy therapy treatment plan to be a proton therapy treatment plan. It will be understood, however, that these teachings will accommodate other approaches.

These teachings will accommodate a variety of ways to present that linear energy transfer information 202. For example, such information can be provided using alphanumeric content and/or graphic content (where different levels are illustrated, for example, via color or grayscale selections and/or gradients).

These teachings then provide for detecting (at decision block 203) a user input (again, for example, via the afore-mentioned user interface 103) with respect to that presented linear energy transfer information 202 to provide a corresponding detected user input. (In the absence of detecting a relevant trigger event, this process 200 can accommodate any of a variety of responses. Examples of responses can include temporal multitasking (pursuant to which the control circuit 101 conducts other tasks before returning to again monitor for a trigger event) as well as continually looping back to essentially continuously monitor for the trigger event(s). These teachings will also accommodate supporting this detection activity via a real-time interrupt capability.)

That detected user input may comprise, for example, user-based cursor movement. Such a cursor movement may correspond, for example, to user-based painting of a displayed patient portion (such as all or part of a treatment target and/or one or more organs-at-risk). That painting can serve, for example, to select the painted area/volume for subsequent consideration/treatment per these teachings.

Figure 3:
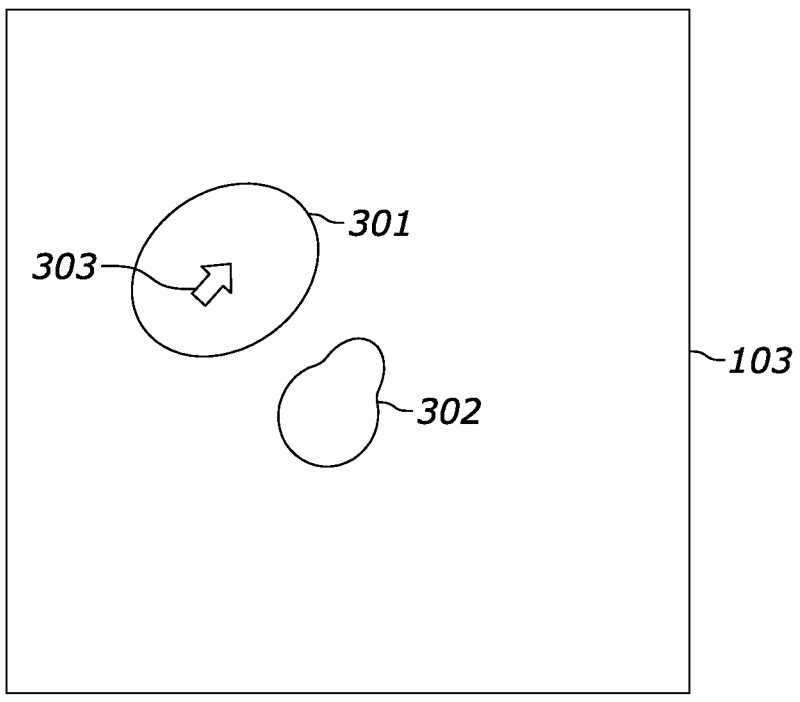
FIG. 3 comprises a screen shot as configured in accordance with various embodiments of these teachings.
Figure 4:
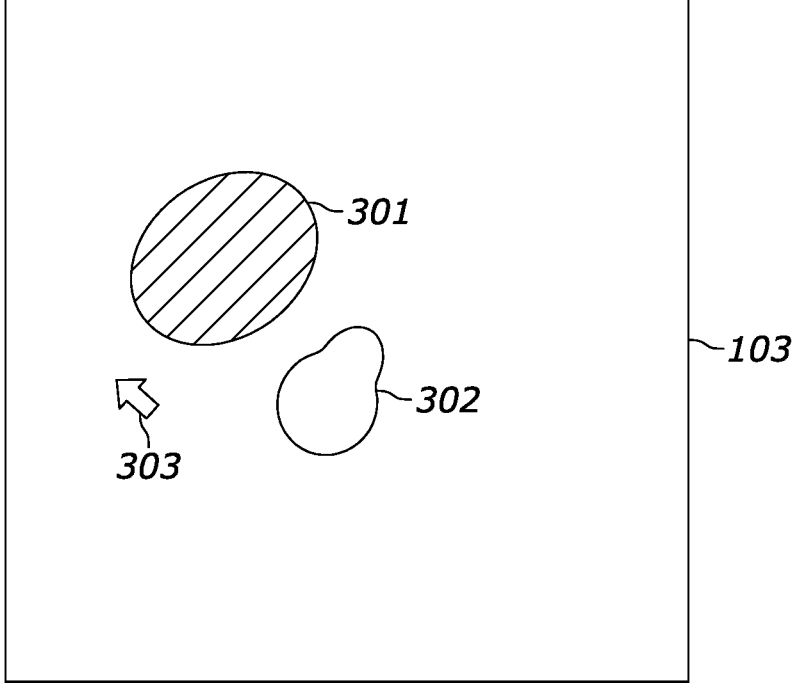
FIG. 4 comprises a screen shot as configured in accordance with various embodiments of these teachings.

FIGS. 3 and 4 present a simple illustrative example in these regards. In FIG. 3, the user interface 103 presents a target volume 301 and an organ-at-risk 302. The user has moved the screen cursor 303 into a position where, by double clicking a mouse button, the entire target volume 301 is selected/painted as shown in FIG. 4.

As another example, in lieu of the foregoing or in combination therewith, the detected cursor movement may correspond to modification of one or more spots, thereby resulting in at least one detected spot-based modification. Those skilled in the art will know that in proton radiation therapy, a "spot" refers to a specific location within a tumor (or other volume of interest) that is targeted with a precise beam of proton radiation.

In response to detecting the aforementioned user input, at block 204 this process 200 accesses a precomputed influence matrix 205 to provide corresponding resultant accessed information. By one approach, the foregoing precomputed influence matrix 205 comprises, at least in part, precomputed linear energy transfer information (which is, to be clear, not necessarily identical to the previously-mentioned linear energy transfer information 202).

By one approach, this precomputed influence matrix 205 comprises precomputed linear energy transfer contributions. As used herein, this reference to "precomputed" shall be understood to mean computations that were undertaken and completed prior to the time of need. By one approach, this can mean at a time prior to instigation of this process 200.

As one illustrative example in these regards, these contributions might comprise a precomputed linear energy transfer contribution for a particular voxel, or precomputed linear energy transfer contributions to each of a plurality of voxels (such as each voxel that corresponds to the user selection referred to above). By one approach, and in the latter regard, the precomputed influence matrix 205 may comprise each spot's precomputed linear energy transfer contributions for each voxel. (In three-dimensional computer graphics, a voxel represents a value on a regular grid in three-dimensional space. In radiation treatment planning, medical imaging data such as that which is obtained through computed tomography scans can be used to create a detailed three-dimensional model of a patient's anatomy. Each voxel in such a model can also hold information about such things as the density and composition of the underlying tissue at that specific location.)

By one approach, the contents of the precomputed influence matrix 205 can be computed by storing each spot's linear energy transfer to each voxel. This approach allows these stored contributions to be accessed quickly at a time of need and without need to recalculate such information every time something changes in the developing plan.

At block 206, the control circuit 101 can then present modified linear energy transfer information via the user interface 103 as a function, at least in part, of the aforementioned accessed information. So configured, the user can view, for example, linear energy transfer contributions that were accessed from the precomputed influence matrix 205. The foregoing may comprise, for example, having a user select (for example, by painting) a greater (or lesser) level of linear energy transfer (or dose) for a particular patient region, and then reacting automatically by quickly presenting such things as the resulting spot weights, linear energy transfer, and so forth. As another example, these teachings will accommodate having the user edit spot weights and dosing and then automatically updating and presenting the resultant linear energy transfer results.

Because the presented information was precomputed, this entire process can be completed in essentially real time (in that, to the user, the foregoing activities can appear to take place instantaneously). As a result, these teachings will accommodate allowing the user to repeat blocks 201 through 206 any number of times (for example, to test various linear energy transfer levels with various portions of the patient's anatomy) without any undue time consequences, thereby allowing the user the freedom to explore options while making useful, thoughtful observations of the attending potential consequences and/or results of those options.

At optional block 207, these teachings will accommodate completing optimization of the energy therapy treatment plan to provide an optimized energy therapy treatment plan 113. At block 208, these teachings will then accommodate administering therapeutic energy to a corresponding patient 104 as a function of the optimized energy therapy treatment plan 113 using, for example, the corresponding energy treatment platform 114.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method comprising:
by a control circuit:
    presenting, via a user interface, linear energy transfer information that corresponds to optimizing an energy therapy treatment plan;
    detecting a user input via the user interface, to provide detected user input;
    in response to the detected user input, accessing a precomputed influence matrix to provide accessed information;
    presenting modified linear energy transfer information via the user interface as a function, at least in part, of the accessed information.

2. The method of claim 1 wherein the energy therapy treatment plan comprises a proton therapy treatment plan.

3. The method of claim 1 wherein detecting the user input via the user interface comprises, at least in part, detecting cursor movement.

4. The method of claim 1 wherein detecting the user input via the user interface comprises, at least in part, detecting user-based painting of a displayed patient portion.

5. The method of claim 1 wherein detecting the user input via the user interface comprises, at least in part, detecting at least one spot-based modification.

6. The method of claim 1 wherein the precomputed influence matrix comprises precomputed linear energy transfer contributions.

7. The method of claim 6 wherein the precomputed linear energy transfer contributions comprise precomputed linear energy transfer contributions for each voxel.

8. The method of claim 7 wherein the precomputed linear energy transfer contributions for each voxel comprise each spot's linear energy transfer contributions for each voxel.

9. The method of claim 1 further comprising:

completing optimization of the energy therapy treatment plan to provide an optimized energy therapy treatment plan.

10. The method of claim 9 further comprising:

administering therapeutic energy to a patient as a function of the optimized energy therapy treatment plan.

11. An apparatus comprising:

a memory having a precomputed influence matrix stored therein;

a user interface;

a control circuit operably coupled to the memory and the user interface and configured to:

present, via the user interface, linear energy transfer information that corresponds to optimizing an energy therapy treatment plan;

detect a user input via the user interface, to provide detected user input;

in response to the detected user input, accessing the precomputed influence matrix to provide accessed information;

present modified linear energy transfer information via the user interface as a function, at least in part, of the accessed information.

12. The apparatus of claim 11 wherein the energy therapy treatment plan comprises a proton therapy treatment plan.

13. The apparatus of claim 11 wherein the control circuit is configured to detect the user input via the user interface by, at least in part, detecting cursor movement.

14. The apparatus of claim 11 wherein the control circuit is configured to detect the user input via the user interface by, at least in part, detecting user-based painting of a displayed patient portion.

15. The apparatus of claim 11 wherein the control circuit is configured to detect the user input via the user interface by, at least in part, detecting at least one spot-based modification.

16. The apparatus of claim 11 wherein the precomputed influence matrix comprises precomputed linear energy transfer contributions.

17. The apparatus of claim 16 wherein the precomputed linear energy transfer contributions comprise precomputed linear energy transfer contributions for each voxel.

18. The apparatus of claim 17 wherein the precomputed linear energy transfer contributions for each voxel comprise each spot's linear energy transfer contributions for each voxel.

19. The apparatus of claim 11 wherein the control circuit is further configured to:

complete optimization of the energy therapy treatment plan to provide an optimized energy therapy treatment plan.

20. The apparatus of claim 19 further comprising:

a radiation treatment platform configured to administer therapeutic energy to a patient as a function of the optimized energy therapy treatment plan.

* * * * *